United States Patent
Latiolais

(10) Patent No.: US 8,376,744 B2
(45) Date of Patent: Feb. 19, 2013

(54) ROTARY GINGIVAL CORD PACKER

(76) Inventor: Lon Jude Latiolais, Georgetown, TX (US)

( * ) Notice: Subject to any disclaimer, the term of this patent is extended or adjusted under 35 U.S.C. 154(b) by 344 days.

(21) Appl. No.: 12/589,962

(22) Filed: Oct. 30, 2009

(65) Prior Publication Data

US 2010/0062393 A1    Mar. 11, 2010

Related U.S. Application Data

(63) Continuation-in-part of application No. 12/283,104, filed on Sep. 9, 2008, now abandoned.

(51) Int. Cl.
*A61C 3/00* (2006.01)

(52) U.S. Cl. .......... 433/141; 433/214

(58) Field of Classification Search .......... 433/141–145, 433/136, 138, 146, 163–166, 214, 215, 229; 33/513–514; 606/180, 170, 176
See application file for complete search history.

(56) References Cited

U.S. PATENT DOCUMENTS

| | | | |
|---|---|---|---|
| 150,943 A * | 5/1874 | Dennet | 433/164 |
| 3,985,147 A | 10/1976 | Ricketts et al. | |
| 4,396,375 A | 8/1983 | Gores | |
| 4,559,957 A | 12/1985 | Hokama | |
| 4,887,598 A | 12/1989 | Berke | |
| 5,022,859 A | 6/1991 | Olivia | |
| 5,104,317 A * | 4/1992 | Riazi | 433/136 |
| 5,718,583 A | 2/1998 | Flanagan | |
| 6,024,564 A | 2/2000 | Kesling | |
| 7,033,173 B2 * | 4/2006 | Coopersmith | 433/136 |
| 2002/0151919 A1 | 10/2002 | Love et al. | |
| 2005/0130099 A1 | 6/2005 | Besek et al. | |

FOREIGN PATENT DOCUMENTS

WO    WO 2007/115063 A2 *  10/2007

* cited by examiner

*Primary Examiner* — Cris L Rodriguez
*Assistant Examiner* — Edward Moran
(74) *Attorney, Agent, or Firm* — The Matthews Firm

(57) ABSTRACT

A dental apparatus usable to place cord beneath a gum line and related methods of use are disclosed herein. The apparatus includes a handle having one or more rotary members attached thereto. In operation, the edge of a rotary member is placed in contact with a cord surrounding a tooth, and the edge is rolled along the length of the cord, such that contact between the edge and the cord causes the rotary member to rotate, while the other portions of the apparatus are moved laterally during use. The cord is thereby placed beneath the gum line while contact between the apparatus and surrounding teeth and gums is minimized.

8 Claims, 4 Drawing Sheets

ROTARY GINGIVAL CORD PACKER

CROSS REFERENCE TO RELATED APPLICATIONS

The present application is a continuation-in-part application, which claims priority to the United States patent application having the application Ser. No. 12/283,104, filed Sep. 9, 2008 now abandoned, the entirety of which is incorporated herein by reference.

FIELD

The present invention relates, generally, to a dental apparatus for placing cord beneath a gum line and related methods of use, and further, to an improved gingival cord suitable for retracting gingival tissue from a tooth.

BACKGROUND

When performing restorative dental procedures or other dental operations, it is often necessary to obtain an impression of one or more teeth. To obtain a suitable impression of a tooth, impression material must be able to flow slightly beneath the gum line.

Typically, gingival tissue, saliva, and/or gingival bleeding can block access of the impression material to portions of the tooth below the gum line. A gingival cord can be used to temporarily retract portions of the gum from one or more teeth to ensure access of the impression material to all necessary portions of the tooth. A conventional gingival retraction cord is round in cross-section, formed from braided and/or woven cotton or other absorbent materials, which are often dipped in or impregnated with a substance to control bleeding or moisture. The cord is looped closely around a tooth, and must then be packed around the base of the tooth to separate the gingival tissue from the tooth.

Conventionally, this cord-packing procedure is performed using a narrow dental instrument with a blunted tip to forcefully push the cord between the tooth and gum tissue, compressing the cord to cause formation of a temporary gap between the tooth and surrounding gum tissue. Use of a conventional gingival cord packing tool can be a time-intensive process, can cause discomfort to a patient, and can cause trauma and damage to the tooth and/or the gum. Damaged gum tissue can bleed, hindering the ability of impression material to flow below the gum line to obtain an impression of the tooth. Further, damaged gum tissue can recede, causing sensitive areas of the tooth to become exposed and hindering the effectiveness of restorative dental procedures, such as crowns and bridges.

Other instruments used to pack a cord into the gingival tissue surrounding a tooth include tools having narrow members that slide or scrape along the surface of a tooth, which can cause discomfort or pain, and can also cause damage to the tooth and surrounding gum tissue.

A need exists for a dental apparatus that is usable to place cord beneath a gum line quickly, without causing trauma or discomfort.

A further need exists for a dental apparatus that can gently move along the length of a cord around a tooth while eliminating scraping and minimizing contact with the tooth, thereby minimizing the possibility of damage or discomfort to the patient.

A need also exists for a dental apparatus that can quickly and efficiently place a cord beneath a gum line, without requiring time-intensive packing or scraping methods.

A need exists for a gingival cord having an advantageous cross-sectional shape that does not require significant packing or compression to retract gingival tissue from a tooth, thereby greatly minimizing trauma and/or damage to gum tissue during a cord packing procedure and discomfort to a patient.

The present invention meets these needs.

SUMMARY

The present invention relates, generally, to a dental apparatus for placing cord beneath a gum line, and to an improved gingival cord usable to retract gingival tissue from a tooth for use with the dental apparatus.

Rather than forcefully packing and/or pushing a cord between a tooth and the surrounding gingival tissue, the present invention utilizes a rotary member to contact the cord. As the edge of the rotary member is moved along the cord, the rotary member rotates while the cord is gently placed between the tooth and surrounding tissue.

In a specific embodiment of the present invention, the apparatus can include a handle member, having a rotary member in communication with one or both ends of the handle. A shank can be fixedly or removably connected to an end of the handle member, with a rotary member rotatably connected to the end of the shank. The shank can have any shape or configuration, including a straight or angled orientation, and typically has a diameter less than that of the handle member. In an embodiment of the invention, the shank can be angled to facilitate access of the rotary member to the gingival tissue without impacting a tooth or other portions of the oral cavity.

In a preferred embodiment of the invention, the apparatus includes an elongate handle having an angled shank disposed on each end. The angled shanks can be selectively oriented to facilitate access to one or more portions of the gum line. The angled shanks can have a diameter less than that of the elongate handle, for facilitating access and maneuverability within the mouth. A circular rotatable member can be connected to the tip of each angled shank. The rotary members can be disposed perpendicularly in relation one another, thereby enabling each end of the apparatus to selectively provide easy access to various portions of the mouth. The angles of each angled shank can be identical, or the angles can be selected such that each shank facilitates access to differing portions of the gum line.

While one embodiment of the invention includes a rotary member having a smooth edge, in an alternate embodiment of the invention, the rotary member(s) can have a modified edge adapted to grip a cord while rolling axially around a tooth. The modified edge can be roughed, serrated, beveled, and/or have other protrusions or features that penetrate slightly into the cord when contacted. Use of a modified edge can prevent slipping of the apparatus and can provide improved effectiveness when placing cord around a tooth.

While all portions of the apparatus can be formed from steel and/or other materials common to dental instruments, in an embodiment of the invention, the rotary member(s), the shank(s), the handle, or combinations thereof can be selectively formed, in whole or in part, from a non-metallic material, such as plastic, for enabling the present apparatus to be used in the vicinity of dental implants and other metallic dental features that can be damaged through contact with mental instruments. The connection between the rotary member and the shank and/or handle can be modified depending on the material used. For example, a plastic implement would require a greater amount of material at the point of connection between a shank and the rotary member to prevent breakage, while a metal implement could utilize a relatively small amount of material, such as a small pin through a thin plate, and retain sufficient sturdiness.

In a further embodiment of the invention, removable, interchangeable metallic shanks and rotary members, or non-metallic, disposable shanks and rotary members can be provided, for threaded engagement, or other types of engagement, with a reusable handle member. Use of interchangeable shanks and/or rotary members facilitates inexpensive disposal and cleaning/autoclaving, as well as allowing the apparatus to be adapted for access to multiple teeth and/or gingival regions. For example, shanks having differing angles or configurations specifically adapted for accessing the gum tissue surrounding front or back teeth could be interchangeably used. Similarly, rotary members having differing diameters could be interchanged for placing cord alongside certain teeth. A rotary member having a diameter of about four millimeters is usable for most purposes; however, a smaller rotary member can be of particular use placing cord around smaller front teeth, while a larger rotary member can be used to place cord around molars and other larger teeth.

The rotary members of the present invention are usable to engage and roll along a gingival cord, quickly and efficiently placing the cord beneath a gum line in a single motion. Conversely, conventional packing tools require multiple strokes in a poking or scraping manner to pack a cord into the gum, which is a time consuming process that can cause discomfort and pain to a patient while risking damage to a tooth or the surrounding gingival tissue.

Thus, the rotary members can place the cord beneath the gum line while minimizing the risk of contact with gum tissue, thereby minimizing the risk of patient discomfort, trauma, and/or bleeding. Additionally, the rotary members are usable to place the cord beneath the gum line without contacting the tooth, further reducing patient discomfort and possible damage to the tooth.

The present invention also relates to methods for placing gingival cord beneath a gum line.

After a gingival cord is placed around a tooth, a dental apparatus having a rotary member, as described above, is provided. The edge of the rotary member is placed against the gingival cord, and the edge is then moved along the gingival cord. Contact between the edge of the rotary member and the cord causes the rotary member to rotate, such that the apparatus rolls along the cord, gently placing the cord between the gum tissue and the tooth, rather than forcefully packing the cord into place.

While moving the rotary member along the gingival cord, contact between the rotary member and the tooth can be minimized, thereby preventing patient discomfort and damage to the tooth. Ideally, the dental apparatus can be used to place a cord beneath a gum line while contacting only the cord, without contacting the gums or teeth. Use of a rotary member having a modified edge with serrations and/or other protrusions to penetrate slightly into the cord can facilitate this effectiveness.

When using a dental apparatus having a second rotary member, perpendicularly disposed in relation to the first rotary member, or otherwise positioned with a differing configuration, the method can include selectively using the second rotary member to move along the cord when the angle of the second rotary member would facilitate placement of the cord.

The present invention also relates, generally, to an improved gingival cord usable to retract gingival tissue from a tooth. While conventional gingival retraction cords have a generally round cross-sectional shape, and are made from woven or braided cotton or similar absorbent, compressible materials, the present improved gingival cord is provided with a generally wedge-shaped cross-section, which facilitates penetration and insertion of the cord between a tooth and adjacent gingival tissue without requiring forceful packing or compression of the cord.

In a preferred embodiment of the invention, the cord can have an elongate core having the wedge-shaped cross-section, with an absorbent material disposed about the core. The core can be formed from a laterally flexible, non-compressible material, such as cork, while the absorbent material is formed from cotton or other fabrics and/or textiles, polymers, or similar materials. The non-compressible nature of the core ensures that the wedge-shaped cross-section of the cord remains intact as the cord is placed between a tooth and the surrounding gingival tissue, while the absorbent material provides the cord with a sufficient degree of compression and expansion to effectively retract the gingival tissue and control any bleeding, saliva, or other fluids. In an embodiment of the invention, the cord can be coated with or otherwise combined with a medicated substance, such as an astringent material, and/or substances to control moisture and bleeding.

BRIEF DESCRIPTION OF THE DRAWINGS

In the detailed description of the embodiments of the invention presented below, reference is made to the accompanying drawings, in which.

The depicted embodiments of the invention are described below with reference to the listed Figures.

DETAILED DESCRIPTION OF THE EMBODIMENTS

Before explaining selected embodiments of the invention in detail, it is to be understood that the present invention is not limited to the particular embodiments depicted and/or described and that the present invention can be practiced or carried out in various ways.

Figure 1:
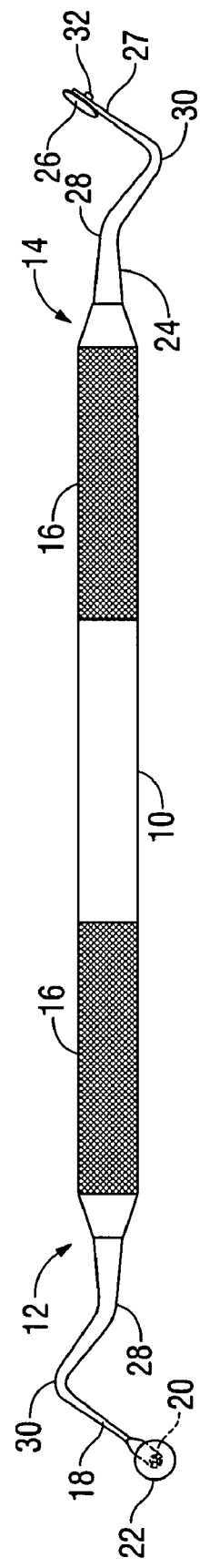
FIG. 1 depicts a side view of an embodiment of the present dental apparatus.

Referring now to FIG. 1, a side view of an embodiment of the present dental apparatus is depicted.

FIG. 1 depicts an elongate handle (10) having a first end (12) and a second end (14). The elongate handle (10) is shown having a generally cylindrical shape with frustoconical ends and knurled areas (16) for facilitating manual manipulation of the apparatus. Other types of grip and/or non-slip surfaces can also be used in addition to or in lieu of the knurled areas (16). In an embodiment, the elongate handle (10) can be approximately 10.8 centimeters in length and about 0.6 centimeters in diameter. However, it should be noted that the dimensions of the present dental apparatus can vary depending on the preferences of the dentist, features of the tooth or patient, location of the tooth within the mouth, or other characteristics.

A first angled shank (18) is shown connected to the first end (12) of the elongate handle (10). The first angled shank (18) has a tip (20), which is connected to a first rotary member (22).

A second angled shank (24) is shown connected to the second end (14). The second angled shank (24) has a tip (27), which is connected to a second rotary member (26).

Each angled shank (18, 24) is depicted having a first angular bend (28) of approximately 150 degrees in relation to the axis of the elongate handle (10), and a second angular bend (30) of approximately 90 degrees in the direction opposite that of the first angular bend. Each angled shank (18, 24) is shown having angular bends in opposition to one another, that position each angled shank (18, 24) with an opposing orientation with respect to the elongate handle (10). However, in an embodiment, the angled shanks (18, 24) can have angular bends that position each angled shank (18, 24) on the same side of the elongate handle (10).

The location of the angular bends (28, 30) and the size of the angles can vary depending on the preferences of the dentist, the shape of a patient's mouth, the location of one or more teeth, or other similar characteristics. The size and location of the angular bends (28, 30) can be selected to facilitate access to various parts of the mouth and gum line. It should be noted that other configurations of the shanks (18, 24) are also usable, including straight members, curved members, members having a single angle, members having more than two angles, or other arrangements.

Each rotary member (22, 26) is depicted having a diameter of approximately 4 millimeters, and a thickness of approximately 1 millimeter, however rotary members of other sizes are also usable. The diameter and/or thickness of the rotary members (22, 26) can be selected to facilitate at least partial entry of the rotary members (22, 26) into spaces between teeth, and based on the size of the tooth around which a gingival cord is to be placed. For example, a rotary member having a diameter smaller than 4 millimeters could be used to place a cord around smaller front teeth, while a rotary member having a diameter larger than 4 millimeters could be used to place a cord around molars and other larger teeth.

The rotary members (22, 26) are shown attached to their respective tips (20, 27) using pins, of which a pin (32) attached to the second tip (27) is visible. The pins (32) provide the rotary members (22, 26) with 360 degrees of free rotation about their central axes, while the attached angled shanks (18, 24) remain stationary or are moved in lateral directions as the apparatus is used. Other fastening members that provide the circular rotatable members (22, 26) with free rotation while the angled shanks (18, 24) remain stationary or move laterally can also be used.

The size of the shanks (18, 14) and the tips (20, 27) to which the rotary members (22, 26) are attached, as well as the size and type of fastener or other attachment member used can be varied depending on the material from which the rotary members (22, 26) and/or the shanks (18, 14) are formed. For example, when using disposable plastic shanks and rotary members to avoid causing damage to metallic dental features, the tips (20, 27) would be significantly broad and thick to prevent breakage of the apparatus during use. When using metallic shanks and/or rotary members, less material could be used.

Figure 2:
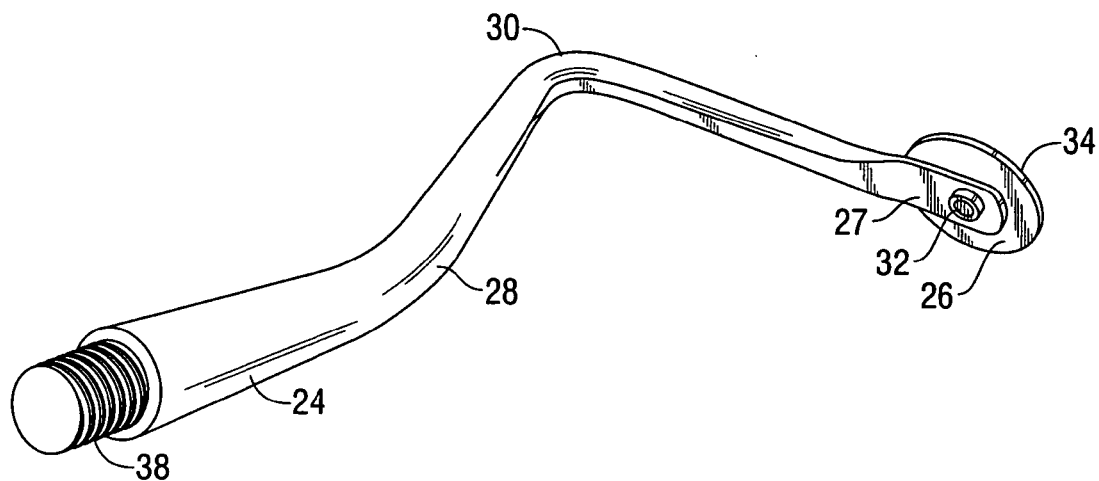
FIG. 2 depicts a perspective view of an embodiment of a first removable end of the present dental apparatus.

Referring now to FIG. 2, a perspective view of a removable end of the dental apparatus of FIG. 1 is shown. Specifically, FIG. 2 depicts an embodiment of the second angled shank (24), having threads (38) for engagement with a handle member. While FIG. 2 depicts the angled shank (24) having exterior threads (38) for engagement with complementary interior threads within a handle member, other configurations of threads and other methods of attachment are also usable.

The second angled shank (24) is depicted having first angled bend (28) and second angled bend (30), as described previously. The second angled shank (24) terminates in a tip (27), which is depicted having a width slightly greater than that of the remainder of the second angled shank (24), and a thickness slightly less than that of the second angled shank (24), for accommodating the pin (32).

The pin (32) is shown, rotatably securing the second rotary member (26) to the second angled shank (24). The pin (32) can be fixed within the tip (27), the second rotary member (26), or combinations thereof, or the pin (32) can be removable to enable the second rotary member (26) to be interchangeably removed from the tip (27) to enable use of differently-sized rotary members and/or to facilitate disposal of disposable portions of the apparatus. The dimensions of the tip (27) and/or the pin (32) can be varied depending on the material used to form the shank (24), tip (27), and/or the pin (32). For example, a shank and tip formed from plastic would have greater dimensions than a shank or tip formed from metal to prevent breakage.

The second rotary member (26) is shown having an edge (34), which is usable to roll along a gingival cord or other surface as the rotary member (26) rotates, while the second angled shank (24) is moved laterally. The edge (34) can thereby be used to move along the length of a gingival cord, whereby the second rotary member (26) is rotated through contact with the gingival cord, without contacting the adjacent gum tissue or tooth. While FIG. 2 depicts the edge (34) as generally smooth, in an embodiment of the invention, the edge (34) can be serrated, roughened, beveled, or combinations thereof, to facilitate a gripping relationship between the edge (34) and a contacted gingival cord, such that protruding portions of the edge (34) penetrate slightly into the surface of the cord.

Figure 3:
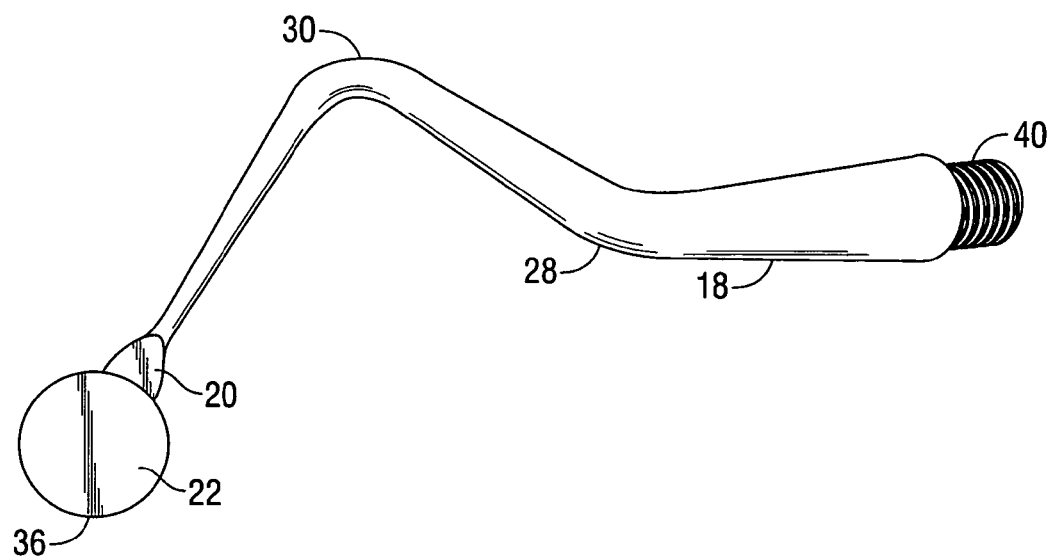
FIG. 3 depicts a perspective view an embodiment of a second removable end of the present dental apparatus.

Referring now to FIG. 3, a perspective view of a second removable end of the dental apparatus of FIG. 1 is shown. Specifically, the first angled shank (18) is depicted, having threads (40) for engagement with a handle member. While FIG. 3 depicts exterior threads (40) for engagement with complementary interior threads within a handle member, other configurations of threads and other methods of attachment are also usable.

The first angled shank (18) is shown having a first angled bend (28) and a second angled bend (30), as described previously. The first angled shank (18) terminates in a tip (20), which can be substantially similar in shape and have substantially similar dimensions to the opposing tip (27, depicted in FIG. 2), and can be perpendicularly disposed in relation to the opposing tip.

The tip (20) accommodates a pin (not visible in FIG. 3), which rotatably secures the first rotary member (22) to the first angled shank (18) in a substantially similar manner to the securing of the second rotary member to the second angled shank, as shown in FIG. 2. The first rotary member (22) can be secured in a perpendicular relationship, or another relationship providing an angle between the rotary members for facilitating access to different sides of a tooth and/or differing portions of the oral cavity. The dimensions of the first angled shank (18), tip (20), and the corresponding pin can vary in the same manner as those of the second angled shank (24), as described above.

The first rotary member (22) has an edge (36), which is usable to roll along a gingival cord or other surface as the first rotary member (22) rotates, while the first angled shank (18) moves laterally. The angled or perpendicular relationship between the first and second rotary members can enable each angled shank to easily reach differing locations around a tooth for placing a cord beneath the gum line. As described previously, the edge (36) can include a smooth edge or a roughened, serrated, beveled, or otherwise modified edge for enhancing the engagement between the edge (36) and a gingival cord.

Figure 4A:
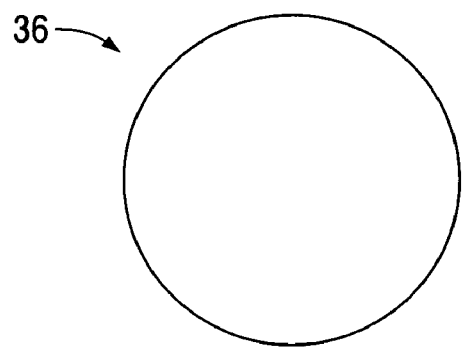
FIGS. 4A and 4B depict embodiments of a rotary member usable with the present invention.
Figure 4B:
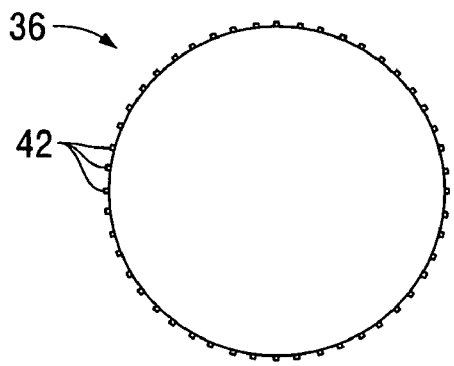

Referring now to FIGS. 4A and 4B, embodiments of a rotary member usable with the present invention are depicted.

FIG. 4A depicts an embodiment of a rotary member having an edge (36) that is generally smooth. A rotary member having a smooth edge can be used to minimize production costs, in situations when avoidance of damage to a braided or woven gingival cord is a concern, or when contact with a tooth or gum tissue is likely due to tooth or gum placement and damage and discomfort to a patient is a concern.

FIG. 4B depicts an embodiment of a rotary member having an edge (36) with a plurality of serrations (42) thereon. The serrations are usable to penetrate slightly within a gingival cord to enhance the grip between the edge (36) and the cord and prevent slipping of the apparatus during use.

Figure 4C:
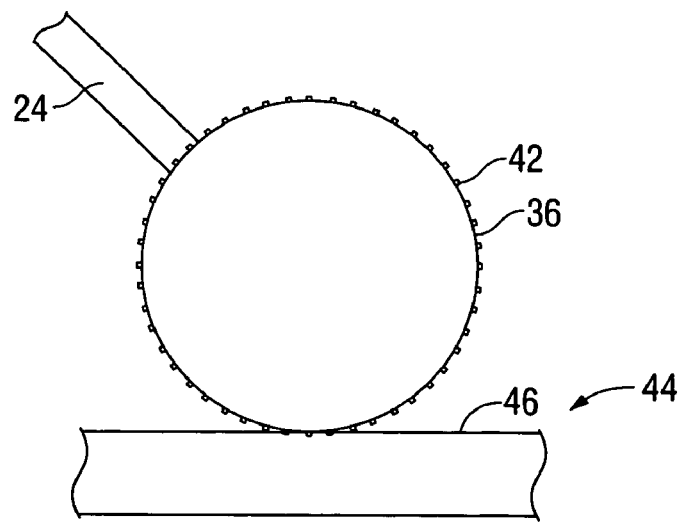
FIG. 4C depicts the rotary member of FIG. 4B engaged with a gingival cord.

FIG. 4C depicts the rotary member of FIG. 4B, having an edge (36) with serrations (42) engaged with a segment of cord (44). The serrations (42) of the rotary member are shown penetrating within the edge (46) of the cord (44) to enhance the engagement therebetween.

While FIGS. 4A, 4B, and 4C depict a rotary member having smooth or serrated edges, other types of modified edges are also usable, such as roughened and/or beveled edges.

Figure 5A:
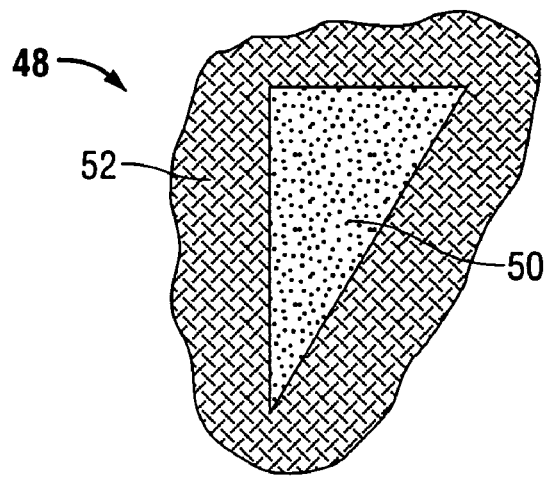
FIG. 5A depicts a cross-sectional view of an embodiment of a gingival retraction cord usable with the present invention.

Referring now to FIG. 5A, a cross-sectional view of an embodiment of a gingival retraction cord (48) is depicted. The gingival retraction cord (48) is shown having a generally triangular, wedge-shaped cross-section provided by a generally rigid core (50). The core (50) can be formed from a laterally flexible, non-compressible material, such as cork or a similar, fairly rigid material.

The core (50) is surrounded by a compressible absorbent material (52), such as cotton, other fabrics or textiles, polymers, or combinations thereof. While the core (50) provides the gingival retraction cord (48) with a constant, generally triangular, wedge-like cross-sectional shape, the compressible absorbent material (52) absorbs saliva and blood from surrounding gingival tissue and enables the gingival retraction cord (48) to compress and expand as needed to enter a space between a tooth and the surrounding gingival tissue. In an embodiment of the invention, the absorbent material (52) can be dipped or otherwise associated with a medical substance, such as an astringent and/or a clotting substance to control bleeding.

Figure 5B:
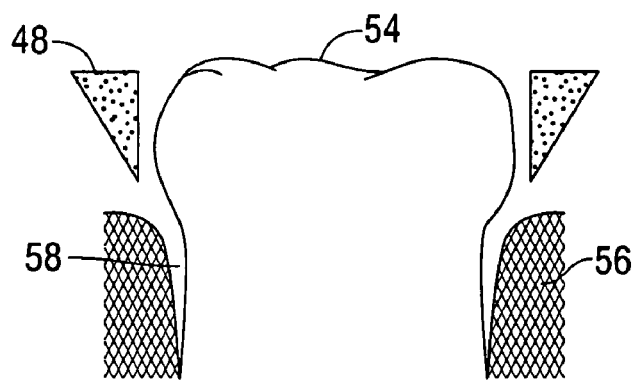
FIG. 5B depicts a cross-sectional view of the gingival retraction cord of FIG. 5A adjacent a tooth from which gingival tissue is to be retracted.

Referring now to FIG. 5B, a cross-sectional view of a tooth (54), surrounded by adjacent gingival tissue (56), is shown. The tooth (54) and gingival tissue (56) define a space (58) therebetween. The space (58) is generally triangular. Conventional gingival retraction cords have a round cross-sectional shape and must be forced, packed, and compressed into the generally triangular space (58) to retract the gingival tissue (56) from the tooth (54). The wedge-like cross-sectional shape of the depicted gingival retraction cord (48) facilitates entry of the cord (48) into the space (58) to retract the gingival tissue (56).

Figure 5C:
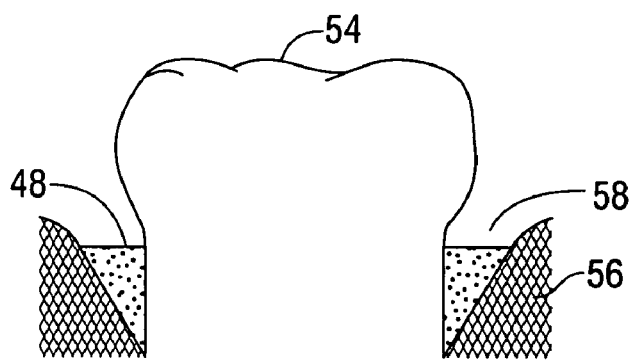
FIG. 5C depicts a cross-sectional view of the gingival retraction cord of FIG. 5A engaged with the tooth of FIG. 5B.

Referring now to FIG. 5C, the gingival retraction cord (48) is shown engaged between the tooth (54) and the gingival tissue (56), thereby retracting the gingival tissue (56) in a manner suitable to permit impression material to flow along the tooth (54) below the gumline. The wedge-shaped cross-section of the retraction cord (48), combined with the stiffness of the cord (50, depicted in FIG. 5A) enables the cord (48) to more readily enter the space (58) without requiring the substantial, forceful packing normally required to force a gingival cord having a round cross-sectional shape into the generally triangular space (58).

The present invention thereby provides a dental apparatus usable to place cord beneath a gum line quickly, without contacting the adjacent tooth or gingival tissue, by moving a rotary member along the cord. The present invention overcomes the deficiencies of conventional methods, which involve forcibly packing a cord into the space between a tooth and the surrounding gingival tissue using numerous thrusts from a blunted instrument.

The present invention further provides an improved gingival retraction cord that reduces the required amount and intensity of packing required to place a cord beneath a gum line through use of a non-compressible, generally triangular, wedge-shaped cross-sectional shape. The present invention thereby overcomes the deficiencies of conventional round cords, which must be forcibly compressed by a packing tool to be placed into the generally triangular space between a tooth and adjacent gingival tissue.

While the present invention has been described with emphasis on specific embodiments, it should be understood that within the scope of the appended claims, the present invention can be practiced other than as specifically described herein.

What is claimed is:

1. A method for placing gingival cord beneath a gum line, the method comprising the steps of:
    placing a gingival cord around a tooth;
    contacting an edge of a rotary member with a gingival cord; and
    rolling the edge along the gingival cord while minimizing contact between the rotary member and the tooth, wherein contact between the edge and the gingival cord causes the rotary member to rotate while placing the gingival cord beneath the gum line.

2. The method of claim 1, wherein the edge comprises at least one protruding feature, and wherein the step of contacting the edge of the rotary member with the gingival cord comprises penetrating the at least one protruding feature at least partially into the gingival cord.

3. A method for placing gingival cord beneath a gum line, the method comprising the steps of:
    providing a gingival retraction cord, wherein the gingival retraction cord comprises a generally wedge-shaped cross section comprising a broad end and a narrow end adapted for penetration between a tooth surface and a region of gingival tissue;
    placing the gingival retraction cord around a tooth with the narrow end adjacent to the tooth and a surrounding region of gingival tissue; and
    contacting an edge of a rotary member with the gingival retraction cord causing the rotary member to rotate; and
    applying a force to the broad end of the gingival retraction cord using the edge of the rotary member while minimizing contact between the rotary member and the tooth, thereby causing the narrow end to penetrate between the region of gingival tissue and the tooth and retract the gingival tissue from the tooth.

4. The method of claim 3, wherein the step of applying a force to the broad end of the gingival retraction cord using the edge of the rotary member comprises:

rolling the edge along the gingival retraction cord, wherein contact between the edge and the gingival retraction cord causes the rotary member to rotate while placing the gingival retraction cord beneath the gum line.

5. A method for placing gingival cord beneath a gum line, the method comprising the steps of:
   placing a gingival cord around a tooth;
   providing a dental apparatus comprising a first circular rotatable member connected to the tip of a first angled shank;
   placing an edge of the first circular rotatable member against the gingival cord; and
   rolling the edge along the gingival cord while minimizing contact between the first circular rotatable member and the tooth, wherein contact between the edge and the gingival cord causes the first circular rotatable member to rotate, thereby placing the gingival cord beneath the gum line.

6. The method of claim 5, wherein the dental apparatus further comprises a second circular rotatable member connected to the tip of a second angled shank, wherein the first circular rotatable member is perpendicularly disposed in relation to the second circular rotatable member, and wherein the method further comprises the steps of placing the edge of the second circular rotatable member against the gingival cord and moving the second circular rotatable member along the gingival cord.

7. The method of claim 5, wherein the step of rolling the edge along the gingival cord comprises maintaining the edge in continuous contact with the gingival cord.

8. The method of claim 5, wherein the step of rolling the edge along the gingival cord comprises moving the dental apparatus in a lateral direction.

* * * * *